United States Patent
Damireddi et al.

(10) Patent No.: US 9,567,405 B2
(45) Date of Patent: Feb. 14, 2017

(54) METHOD OF SYNTHESISING SULFORAPHANE

(71) Applicant: PharmAgra Labs, Inc., Brevard, NC (US)

(72) Inventors: Sahadeva Reddy Damireddi, Brevard, NC (US); Kpakpo Ambroise Akue, Asheville, NC (US); Jared K. Nelson, Pisgah Forest, NC (US); Albert Roger Frisbee, Hendersonville, NC (US); Peter Wyatt Newsome, Horseshoe, NC (US)

(73) Assignee: PharmAgra Labs, Inc., Brevard, NC (US)

( * ) Notice: Subject to any disclaimer, the term of this patent is extended or adjusted under 35 U.S.C. 154(b) by 0 days.

(21) Appl. No.: 14/404,773

(22) PCT Filed: May 31, 2013

(86) PCT No.: PCT/GB2013/051458
§ 371 (c)(1),
(2) Date: Dec. 1, 2014

(87) PCT Pub. No.: WO2013/179057
PCT Pub. Date: Dec. 5, 2013

(65) Prior Publication Data
US 2015/0191551 A1    Jul. 9, 2015

Related U.S. Application Data

(60) Provisional application No. 61/654,277, filed on Jun. 1, 2012.

(51) Int. Cl.
| | |
|---|---|
| *C07C 315/02* | (2006.01) |
| *C08B 37/16* | (2006.01) |
| *A61K 47/48* | (2006.01) |
| *A61K 31/26* | (2006.01) |
| *A61K 31/724* | (2006.01) |
| *C07C 331/20* | (2006.01) |
| *C08L 5/16* | (2006.01) |
| *B82Y 5/00* | (2011.01) |

(52) U.S. Cl.
CPC ........... *C08B 37/0015* (2013.01); *A61K 31/26* (2013.01); *A61K 31/724* (2013.01); *A61K 47/48969* (2013.01); *B82Y 5/00* (2013.01); *C07C 315/02* (2013.01); *C07C 331/20* (2013.01); *C08L 5/16* (2013.01)

(58) Field of Classification Search
None
See application file for complete search history.

(56) References Cited

U.S. PATENT DOCUMENTS

| | | |
|---|---|---|
| 7,879,822 B2 | 2/2011 | Dagan et al. |
| 2006/0135618 A1 | 6/2006 | Jean et al. |
| 2008/0176942 A1* | 7/2008 | Dagan .................... A61K 31/26 514/514 |

FOREIGN PATENT DOCUMENTS

| | | |
|---|---|---|
| CN | 102249968 A | 11/2011 |
| CN | 102423492 A | 4/2012 |
| CN | 102688219 A | 9/2012 |
| WO | 2008008954 A2 | 1/2008 |
| WO | 2008015315 A1 | 2/2008 |
| WO | 2008091608 A1 | 7/2008 |

OTHER PUBLICATIONS

Wu, Carbohydrate Polymers 82 (2010) 613-617.*
Holland, Tetrahedron: Asymmetry vol. 6, No. 7, pp. 1569-1574, 1995.*
Chen et al. "New Method for the Synthesis of Sulforaphane and Related Isothiocyanates." Synthesis. 24(2011):3991-3996.
Conaway et al. "Phenetyl Isohtiocyanate and Sulforaphane and their N-Acetylcysteine Conjugates Inhibit Malignant Progression of Lung Adenomas Induced by Tobacco Carcinogens in A/J Mice." Cancer Res. 65.18(2005):8548-8557.
Ding et al. "A Facile and Green Synthesis of Sulforaphane." Chinese Chem. Lett. 17.9(2006):1152-1154.
D'Souza et al. "A Facile and Efficient Synthesis of 14C-labelled Sulforaphane." J. Label. Compd. Radiopharm. 46(2003):851-859.
Holland et al. "Biotransform of Organic Sulfides. Part 7. Formation of Chiral Isothiocyanato Sulfoxides and Related Compounds by Microbial Biotransformation." Tetrahed. Asymm. 6.7(1995):1569-1574.
Kelloff et al. "Progress in Cancer Chemoprevention: Development of Diet-Derived Chemopreventive Agents." J. Nutr. 130. S2(2000):467S-471S.

(Continued)

*Primary Examiner* — Layla Berry
(74) *Attorney, Agent, or Firm* — Burns & Levinson LLP; Shawn P. Foley

(57) ABSTRACT

The present invention relates to a method of synthesizing sulforaphane by reacting a compound of formula (A) with an oxidizing agent in an aqueous solvent and in the presence of a catalyst. The invention further provides a method of synthesizing a stabilized complex of sulforaphane and cyclodextrin by mixing the sulforaphane prepared by the methodology defined herein with cyclodextrin in an aqueous solvent.

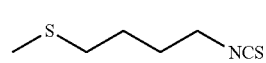

A

29 Claims, No Drawings

(56) References Cited

OTHER PUBLICATIONS

Kuhnert et al. "Synthesis of 1, 1', 2, 2', 3, 3', 4, 4'-Octadeutero-Sulforaphane." J. Label Compd. Radiopharm. 47(2004):501-507.
Mays et al. "Identification, Synthesis, and Enzymology of Non-natural Glucosinolate Chemopreventive Candidates." ChemBioChem. 9(2008):729-747.
Moon et al. "Analysis of Anti-Helicobacter Activity of Sulforaphane and Related Compounds Present in Broccoli (*Brassica oleracea* L.) Sprouts." J. Agric. Food Chem. 58(2010):6672-6677.
Papi et al. "Cytotoxic and Antioxidant Activity of 4-Methylthio-3-butenyl Isothiocyanate from *Raphanus sativus* L. (Kaiware Dalkon) Sprouts." J. Agric. Food Chem. 56(2008):875-883.
Schmid et al. "Synthesis of the Racemic and Optically Active Forms of Sulforaphane." Fasoiculus VI. (1948)1497-1505. (German original and English translation).
Vermeulen et al. "Synthesis of Isothiocyanate-Derived Mercapturic Acids." Eur. J. Med. Chem. 38(2003):729-737.
Wu et al. "Preparation and Stability Investigation of the Inclusion Complex of Sulforaphane with Hydroxypropoyl-β-Cyclodextrin." Carbo. Poly. 82(2010):613-617.

\* cited by examiner

METHOD OF SYNTHESISING SULFORAPHANE

CROSS-REFERENCE TO PRIORITY APPLICATIONS

The present application is a national phase entry under 35 U.S.C. §371 of International Application No. PCT/GB2013/051458 filed May 31, 2013, published in English, which claims priority from U.S. 61/654,277, filed Jun. 1, 2012, all of which are incorporated herein by reference.

FIELD OF THE INVENTION

The present invention relates to a method of synthesising sulforaphane. The present invention also relates to a method of synthesising a stabilised sulforaphane-cyclodextrin complexes.

BACKGROUND OF THE INVENTION

According to the US National Cancer Institute, sulforaphane is considered to be one of the 40 most promising anticancer agents (Kelloff G. J, Crowell J. A, Steele V. E, Lubet R. A, Malone W. A, Boone C. W, Kopelovich L, Hawk E. T, Lieberman R, Lawrence J. A, Ali I, Viner J. L, Sigman C. C, J. Nutr, 2000, 130, 467). It is also known to possess antimicrobial properties. Sulforaphane has therefore attracted interest as a potential agent for the treatment and/or prevention of cancer and microbial infections.

Sulforaphane is found in the cruciferous vegetables such as cabbage, broccoli, broccoli sprouts, brussel sprouts, cauliflower, cauliflower sprouts, bok choy, kale, collards, arugula, kohlrabi, mustard, turnip, red raddish, and water cress. In the plant, it is present in bound form as glucoraphanin, a glucosinolate. In nature, sulforaphane is often formed from glucoraphanin following plant cell damage by an enzymatic reaction.

Various synthetic methods of producing sulforaphane are known in the art. Sulforaphane was synthesized as early as 1948 by Schmid and Karrer (Schmid H. And Karrer, P.; *Helvetica Chimica Acta*. 1948; 31; 6: 1497-1505). The Schmid synthesis results in a racemic mixture.

Various alternative synthetic procedures have been reported by, for example, Vermeulen and co-workers (Vermeulen M, Zwanenburg B, Chittenden G. J. F, Verhagen H, Eur. J. Med. Chem, 2003, 38(78), 729-737), Conaway and co-workers ((Conaway C. C, Wang C. X, Pittman B, Yang Y. M, Schwartz J. E, Tian D, McIntee E. J, Hecht S. S, Chung F. L, Cancer Research, 2005, 65(18), 8548-8557), Kuhnert and co-workers (Kuhnert N and Lu Y, Journal of Labelled Compounds & Radiopharmaceuticals 2004, 47(8), 501-507), Rajski and co-workers (Mays J. R and Rajski, S. R. Chem Bio Chem, 2008, 9(5), 729-747 and WO2008/008954), Christopher and co-workers (Christopher A. D'Souza, Shantu Amin, Dhimant Desai, Journal of Labelled Compounds & Radiopharmaceuticals, 2003, 46(9), 851-859), Takayuki and co-workers (Joon-Kwan M, Jun-Ran K, Young-Joon A and Takayuki S, Journal of Agricultural and Food Chemistry 2010, 58 (11), 6672-6677), and Rabhi and co-workers (WO 2008015315 and U.S. Pat. No. 0,135,618 A1), Cao and his co-workers (Tong Jian Ding, Ling Zhou, Xiao Ping Cao, Chinese Chemical Letters, 2006, 17(9), 1152-1154) and Chen and co-workers (Xin Chen, Zhengyi Li, Xiaoqiang Sun, Hongzhao Ma, Xiaoxin Chen, Jie Ren, Kun Hu, *Synthesis*, 2011, 24, 3991-3996 and CN 102249968).

Although sulforaphane has been synthesized by various different methods, most of the reported methods suffer several drawbacks; such as, for example, low yields, the use of hazardous and potentially harmful reagents (such as thiophosgene which is a highly toxic and volatile liquid with an unpleasant and irritating odour), the use of Class I or II solvents, laborious work-up/purification procedures and unwanted by-products (such as the inseparable disulfone/sulfonyl derivative of sulforaphane). These processes are therefore not suitable for the efficient large-scale synthesis of sulforaphane.

Therefore, there is a need for an alternative process for synthesising sulforaphane which address one or more of the aforementioned drawbacks of the prior art processes. In particular. There is a need for a synthetic process that can be implemented on a large scale. Such a process will ideally be:
  (i) efficient, i.e. it gives commercially viable yields of sulforaphane with good levels of purity and utilises a small number of synthetic steps;
  (ii) cost effective, i.e. utilising low cost reactants and reaction conditions;
  (iii) environmentally acceptable and safe to implement, i.e. it does not use overly toxic reagents or solvents.

One further and significant problem associated with sulforaphane is its inherent instability. Sulforaphane exists in the form of an unstable oil which rapidly degrades under normal conditions. This makes sulforaphane exceptionally hard to manufacture and distribute.

Therefore, there is also a need for a process of synthesising sulforaphane that is readily amenable to subsequent processing steps to provide a more stable form of the sulforaphane that is produced.

One particularly effective approach to stabilise sulforaphane involves the formation of sulforaphane-cyclodextrin complexes. In this regard, U.S. Pat. No. 7,879,822B2, the entire contents of which are hereby incorporated by reference, describes the preparation of sulforaphane-cyclodextrin complexes having good stability.

It therefore a further object of the present invention to provide a facile process that enables the sulforaphane that it synthesized to be readily stabilized by the formation of a sulforaphane-cyclodextrin complex.

SUMMARY OF THE INVENTION

According to a first aspect of the present invention, there is provided a method of synthesising sulforaphane, the method comprising:
reacting, in an aqueous solvent, a compound of formula A:

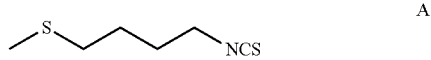

with an oxidizing agent in the presence of a catalyst.

The process of the present invention possesses a number of advantages over conventional prior art methods of producing sulforaphane. Firstly, the process is efficient and provides high yields of the desired sulforaphane end product without significant production of the sulfonyl derivative (Erysolin) as a by-product. Secondly, the reaction can proceed under mild, aqueous conditions. The use of an aqueous solvent, such as water, is particularly advantageous because it avoids the use of expensive and/or potentially hazardous solvents. It also enables the use of less hazardous oxidising agents, such hydrogen peroxide. In addition, the use of an aqueous solvent makes the reaction ideally suited for the quick and efficient in situ formation of stabilised sulforaphane-cyclodextrin complexes (by simply mixing the sulforaphane end product with an aqueous solution of cyclodextrin to form the complex).

The process of the present invention is also suited to large-scale manufacture of sulforaphane.

In another aspect, the present invention relates to sulforaphane formed by, obtainable by, obtained by, or directly obtained by, a process as defined herein.

In yet another aspect, the present invention there is provided a process for the preparation of a complex of sulforaphane and cyclodextrin, the process comprising:
(i) reacting, in an aqueous solvent, a compound of formula A:

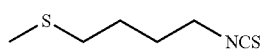

with an oxidizing agent in the presence of a catalyst to form sulforaphane; and
(ii) mixing the sulforaphane from step (i) with cyclodextrin in an aqueous solvent to form a precipitate of the sulforaphane-cyclodextrin complex.

In yet another aspect, the present invention provides a sulforaphane-cyclodextrin complex formed by, obtainable by, obtained by, or directly obtained by, a process as defined herein.

In another aspect, the present invention relates to a sulforaphane-cyclodextrin complex as defined herein for use in the treatment and/or prevention of microbial infections and/or cancer.

In another aspect, the present invention provides a method of treating and/or preventing microbial infections and/or cancer, the method comprising administering to an individual in need of such treatment a therapeutically effective amount of a sulforaphane-cyclodextrin complex as defined herein.

In another aspect, the present invention relates to a pharmaceutical composition comprising a sulforaphane-cyclodextrin complex as defined herein and one or more additional pharmaceutical excipients.

DETAILED DESCRIPTION OF THE INVENTION

Definitions

Unless otherwise stated, the following terms used in the specification and claims have the following meanings set out below.

A "therapeutically effective amount" means the amount of the compound that, when administered to a subject for treating a disease or condition referred to herein, is sufficient to effect such treatment for the disease or condition. The "therapeutically effective amount" will vary depending on the form of the compound (e.g. the salt form), the disease or condition concerned and its severity, as well as the age, weight, etc., of the subject to be treated.

The term "individual" is used herein to mean a warm blooded mammal. Thus, the compound of the present invention may be used for human and/or veterinary applications. In a particular embodiment, the subject is a human.

The term Erysolin is used herein to refer to a compound having the structure shown below:

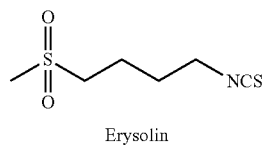

Erysolin

The Process of Producing Sulforaphane

It will be appreciated that, in the description of the synthetic methods described herein, all proposed reaction conditions, including the choice of the aqueous solvent, the reaction atmosphere, the reaction temperature, the duration of the experiment and any workup procedures employed, can be selected by a person skilled in the art. It will also understood by one skilled in the art of organic synthesis that the functionality present on various portions of the molecule must be compatible with the reagents and reaction conditions utilised.

As indicated above, the present invention provides a method of synthesising sulforaphane, the method comprising:

reacting, in an aqueous solvent, a compound of formula A:

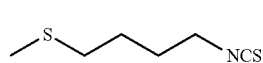

with an oxidizing agent in the presence of a catalyst.

The resultant sulforaphane compound has the structure shown below:

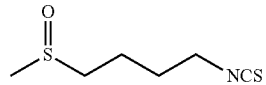

The sulforaphane can be collected and appropriately stored for subsequent use or, more preferably, it can be mixed directly or in situ with cyclodextrin to form a stabilised sulforaphane-cyclodextrin complex as defined further herein. This avoids the need for laborious purifications of the sulforaphane end product.

Any suitable aqueous solvent may be used for the reaction. In an embodiment of the invention, the solvent is water, but mixtures of water and one or more water miscible solvents may also be used in certain circumstances.

Suitably, the aqueous solvent is degassed prior to the reaction. Any suitable procedure known in the art for degassing the aqueous solvent may be used. For example, the solvent may be degassed by sparging the solvent with an inert gas (such as nitrogen or argon), refluxing the solvent, or by utilising vacuum or ultrasonic degassing procedures.

Any suitable oxidising agent may used in the reaction, provided that it is capable of oxidising the compound of formula A to sulforaphane in an aqueous environment. For example, the oxidising agent may be selected from hydrogen peroxide or water soluble or miscible organic per-acids, such as meta-Chloroperoxybenzoic acid (mCPBA). In an embodiment, the oxidising agent is hydrogen peroxide. Hydrogen peroxide is particularly suitable because it reacts in the methodology of the present invention to form sulforaphane and water as the end products (i.e. no unwanted by-products are formed).

Suitably, the oxidising agent is present in an amount sufficient to oxidise all of the compound of formula A to sulforaphane. Typically, about one molar equivalent (relative to the compound of formula A) of the oxidising agent will be required, although it is possible to use a slight excess of the oxidizing agent if the conditions are controlled to prevent or limit the formation of the sulfonyl by-product. For example, in some cases, 1 to 2 molar equivalents of oxidizing agent (relative to the compound of formula A) may be used, more suitably 1 to 1.5 molar equivalents of oxidizing agent is used, and even more suitably 1 to 1.1 molar equivalents of oxidizing agent is used.

The reaction also proceeds in the presence of a suitable catalyst. Any catalyst that is compatible with the aqueous solvent and which is capable of promoting the oxidation of the compound of formula A may be used. The catalyst must be active in the aqueous environment and may be homogeneous or heterogeneous. Examples of suitable catalysts include acid catalysts such as cyclodextrin and/or Fuller's Earth, and organic or inorganic acids, such as, for example, ascorbic acid, formic acid, acetic acid, and/or sulphuric acid.

In a particular embodiment the catalyst is cyclodextrin. Any suitable cyclodextrin may be used as the catalyst. For example, the cyclodextrin may be selected from one or more of W6 (alpha) cyclodextrin (a six sugar ring molecule), W7 (beta) cyclodextrin (a seven sugar ring molecule), W8 (gamma) cyclodextrin (an eight sugar ring molecule), derivatives thereof (such as hydroxyalkyl derivatives, e.g. hydroxypropyl cyclodextrin), and mixtures thereof. Other cyclodextrins known in the art are also contemplated as useful in the synthetic method and the invention shall not be limited to the specific cyclodextrins listed.

In an embodiment of the invention, the cyclodextrin used as a catalyst is alpha-cyclodextrin.

The amount of catalyst required will vary depending on the nature of the oxidizing agent, catalyst and the reaction conditions used. Suitably, 0.0001 to 1.0 molar equivalents of catalyst are present (relative to the compound of formula A) and, more suitably, 0.005 to 0.2 molar equivalents of catalyst are present, and even more suitably, 0.005 to 0.05 molar equivalents of catalyst are present.

In embodiments of the invention where the oxidizing agent is hydrogen peroxide, the hydrogen peroxide is suitably added to the reaction mixture slowly and the temperature of the reaction mixture is maintained at 15° C. or less or, more preferably, 10° C. or less. Suitably, the temperature is monitored during the addition of the hydrogen peroxide and the rate of addition is adjusted to ensure the temperature remains within the desired limits.

In an embodiment of the invention, the oxidizing agent is hydrogen peroxide, the solvent is water, and the catalyst is selected from cyclodextrin, Fuller's Earth, and acids such as ascorbic acid, formic acid, acetic acid, and/or sulphuric acid. In a particular embodiment of the invention, the oxidizing agent is hydrogen peroxide, the solvent is water, and the catalyst is cyclodextrin, particularly α-cyclodextrin. In such embodiments, the compound of formula A and the catalyst may be dissolved in the water and cooled to less than 15° C. or, more preferably, less than 10° C. (for example, between 1 and 2° C.) and the aqueous hydrogen peroxide solution may then added to the cooled solution in a controlled manner so that temperature does not exceed 15° C., or, more preferably, 10° C. The reaction may then be stirred and allowed to proceed for a suitable time, for example between 1 and 48 hours. The sulforaphane product may then be collected or used in subsequent process steps.

The starting material, i.e. the compound of formula A, can be sourced commercially (it can be obtained from various suppliers as either a natural or synthetic product) and/or prepared by techniques known in the art. For example, the compound of formula A may be prepared as an intermediate from a compound of formula B shown below

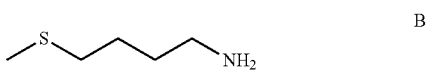

B by procedures described by Vermeulen and co-workers (Eur. J. Med. Chem, 2003, 38(78), 729-737), D'Souza and co-workers (Journal of Labelled Compounds & Radiopharmaceuticals, 2003, 46(9), 851-859), Cao and his co-workers (Chinese Chemical Letters, 2006, 17(9), 1152-1154) and Chen and co-workers (*Synthesis,* 2011, 24, 3991-3996 and CN 102249968).

In an embodiment of the present invention, the compound of formula A is prepared by reacting a compound of the formula B

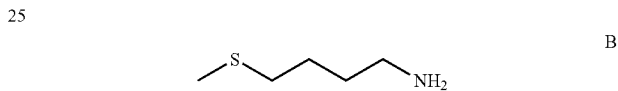

B with carbon disulphide in a suitable solvent (e.g. THF) and in the presence of a suitable base (such as $Et_3N$) and a suitable oxidizing agent (such as hydrogen peroxide).

In a particular embodiment, the solvent is THF, the base is triethylamine, and the oxidizing agent is hydrogen peroxide.

In a further embodiment, the compound of formula B and the base (e.g. triethylamine) are dissolved in a solvent (e.g. THF) at a low temperature (e.g. below 25° C., more preferably below 0° C. and, even more preferably, below −10° C.). Carbon disulphide is then added to the reaction mixture. Suitably the temperature is controlled while the carbon disulphide is added (e.g. it is kept below 25° C., or more preferably below 5° C. and, even more preferably, below 0° C.). Carbon disulphide may be added at a controlled rate in order to keep the temperature of the reaction mixture low (e.g. it may be added drop wise over a period of, for example, 0.5 to 4 hours). The reaction mixture may then be warmed (for example, to between 5 and 25° C., and more preferably to between 5 and 20° C.) and then the oxidizing agent (e.g. hydrogen peroxide) is added.

The resultant crude product of the compound of formula A can be collected, washed and purified (for example by distillation) to give a pure compound of formula A using techniques well known in the art.

The Process of Producing Sulforaphane-Cyclodextrin Complexes

The present invention further provides a process for the preparation of a complex of sulforaphane and cyclodextrin, the process comprising:
(i) reacting, in an aqueous solvent, a compound of formula A:

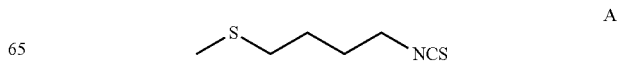

A with an oxidizing agent in the presence of a catalyst to form sulforaphane; and (ii) mixing the aqueous solution of sulforaphane from step (i) with an aqueous solution of cyclodextrin in an aqueous solvent to form a precipitate of the sulforaphane-cyclodextrin complex.

Step (i) of the reaction is the process of synthesising sulforaphane defined above. One particular advantage of using an aqueous solvent in step (i) is that once the reaction is complete, it enables the simple addition of an aqueous solution of cyclodextrin to the reaction mixture in order to form a stabilised sulforaphane-cyclodextrin complex. Therefore, the present process provides a simple, effective and rapid means by which the sulforaphane can be stabilised.

Sulforaphane-cyclodextrin complexes are described in U.S. Pat. No. 7,879,822B2, the entire contents of which are hereby incorporated by reference.

The process of the present invention suitably comprises an additional step of collecting the precipitate of the sulforaphane-cyclodextrin complex and then optionally washing and drying the precipitate. The precipitate may be collected by techniques well known in the art, such as by filtration.

Suitable reaction conditions for forming a sulforaphane-cyclodextrin complex in aqueous solutions are known in the art from U.S. Pat. No. 7,879,822 B2.

In some embodiments, the purity of the resulting complex can be further increased by recrystallization.

Any suitable cyclodextrin may be for forming a complex with the sulforaphane. In embodiments where the catalyst in step (i) is cyclodextrin, then the cyclodextrin used for forming a complex in step (ii) may be the same or different to the cyclodextrin used as a catalyst in step (i). By way of example, the cyclodextrin for use in the methods of the present invention may be selected from one or more of W6 (alpha) cyclodextrin (a six sugar ring molecule), W7 (beta) cyclodextrin (a seven sugar ring molecule), W8 (gamma) cyclodextrin (an eight sugar ring molecule), derivatives thereof (such as hydroxyalkyl derivatives, e.g. hydroxypropyl cyclodextrin), and mixtures thereof. Other cyclodextrins known in the art are also contemplated as useful in the present processes and the invention shall not be limited to the specific cyclodextrins listed.

In an embodiment of the invention, the cyclodextrin used for forming a complex with the sulforaphane in step (ii) is alpha-cyclodextrin.

Prior to mixing with the sulforaphane obtained from step (i), the cyclodextrin utilized in step (ii) of the present method may be dissolved in an aqueous solvent, such as water. The dissolution/dispersion of cyclodextrin in the solvent may be accomplished by any method known in the art. For example, in some embodiments, the cyclodextrin may be fully or partially dissolved in an aqueous solvent by placing the cyclodextrin in the solvent and heating the mixture. In additional embodiments, sonication may be utilized to either fully or partially dissolve the cyclodextrin in the solvent. In further embodiments, multiple methods of dissolution may be utilized to reach the level of dissolution desired by the user, for example, by utilizing sonication in connection with heating the solvent.

Once the sulforaphane and cyclodextrin have been added together in step (ii) of the process, and are ready to be mixed, any method of mixing may be utilized. For example, the components may be mixed by stirring, sonication, agitation, or other methods known in the art. In some embodiments, more than one method of mixing may be utilized together.

The duration of the mixing may vary based on the particular methods of mixing utilized. For example, if stirring or sonication is utilized, the sulforaphane, and cyclodextrin may be mixed for from about 2 hours to about 48 hours. In other embodiments, the sulforaphane and cyclodextrin may be mixed by a stirrer or sonication for about 6 hours to about 15 hours.

As discussed above, multiple methods of mixing may be utilized for mixing the sulforaphane and cyclodextrin. For example, in some embodiments, sonication may be utilized in connection with stirring. In such embodiments, sonication may be utilized for a time period of from about 0.01 hours to about 1.5 hours during mixing with a stirrer for from about 2 hours to about 48 hours.

The initial mixing of the sulforaphane and the cyclodextrin at ambient temperature, for example between 15° C. and 25° C. However, in a particular embodiment, after the sulforaphane and cyclodextrin have been mixed, the mixture is cooled to stabilize the formed precipitate. The particular sulforaphane and cyclodextrin used may dictate the duration and severity of the cooling required. For example, the mixture may be cooled to a temperature within the range of about −10° C. to about 20° C., more suitably between about −8° C. to about 10° C., even more suitably between about −5° C. to about 4° C. The duration of the cooling can vary and may be, for example, from about 0.1 hours to about 24 hours.

In a particular embodiment, the mixture may be cooled to a temperature from about −5° C. to about 2° C., optionally for a time period of about 0.5 hour to about 4 hours. The precipitate may then be filtered to obtain a sulforaphane-cyclodextrin complex of increased purity.

Suitably the molar ratio of sulforaphane to cyclodextrin in the resultant complex is within the range of 0.4:1 to 1:1; suitably 0.8:1 to 1:1; and more suitably 0.9:1 to 1:1, 0.95:1 to 1:1 or 0.98:1 to 1:1.

In further embodiments, the resulting complex may be recrystallized to obtain a complex with an even greater purity level of the sulforaphane. In such embodiments, any method of recrystallization known in the art may be utilized. For example, in some embodiments, recrystallization may be accomplished by cooling the resulting mixture, by dissolving the resulting mixture in a second solvent, through a chemical reaction, by changing the pH of the mixture or by evaporating the solvent. The user's specifications may dictate the particular methods utilized.

In some embodiments, the method of recrystallization may include dissolution of the formed solid particles in a solvent. Such dissolution may be completed by any method known in the art. For example, in some embodiments, the dissolution may be completed through sonication. The sonication may be completed at an elevated temperature, i.e. from about 50° C. to about 100° C., and may be continued until no solid particles remain. Additionally, any solvent known in the art may be utilized, including those indicated above that may be useful in connection with dissolving cyclodextrin.

After dissolution has been substantially completed, the mixture may be held at room temperature to allow the solids to precipitate out of solution. Depending on the materials utilized, the time in which the mixture is held at room temperature may vary. For example, if sulforaphane is utilized, most of the solids may precipitate out of solution within an hour of being held at room temperature. In other embodiments, the solution may take more than or less than an hour to sufficiently allow the solids of the complex to precipitate out of solution.

As discussed above, the solids may then be cooled to aid the formation and stabilization of the complex. The particular complex used may dictate the amount of cooling necessary. For example, in some embodiments, the mixture may be cooled in a cooling device, such as for example a refrigerator, that is maintained at a temperature from about −10° C. to about 20° C., optionally for a time from about 0.1 hours to about 2 hours. In other embodiments, the mixture may be cooled in a cooling device that is maintained at a temperature from about 2° C. to about 6° C. for a time between about 0.5 hours to 1 hour. After the complex has sufficiently crystallized, it may then be filtered to produce a sulforaphane-cyclodextrin complex of even greater purity.

Pharmaceutical Compositions and Methods of Treatment

In another aspect, the invention is directed to a method of providing anticancer and/or antimicrobial treatments to a subject in need of such treatment. The method includes administering to a subject in need of such treatment the sulforaphane-cyclodextrin complexes of increased purity defined herein in a therapeutically effective amount.

A first component of the treatment method is sulforaphane-cyclodextrin complex prepared in accordance with the methods defined herein. The components that are useful in the present invention can be of any purity or grade, as long as the preparation is of a quality and stability suitable for pharmaceutical use and does not affect the resulting preparation's physiological activity or safety.

The method may further include administration of other pharmaceutically acceptable components. The term "pharmaceutically acceptable" is used adjectivally herein to mean that the modified noun is appropriate for use in a pharmaceutical product.

When the sulforaphane-cyclodextrin complex created by the present methods is supplied along with a pharmaceutically acceptable carrier or pharmaceutically acceptable excipient, which terms can be used interchangeably herein, a pharmaceutical composition may be formed. The pharmaceutical compositions of the invention may be prepared by any of the well-known techniques of pharmacy, for example, by admixing the components.

A pharmaceutical composition of the present invention is directed to a composition suitable for the prevention or treatment of the disorders described herein.

Pharmaceutically acceptable carriers and excipients are chosen such that side effects from the pharmaceutical compound(s) are minimized and the performance of the compound(s) is not canceled or inhibited to such an extent that treatment is ineffective. Pharmaceutically acceptable carriers include, but are not limited to, physiological saline, Ringer's, phosphate solution or buffer, buffered saline, and other carriers known in the art. Pharmaceutical compositions may also include stabilizers, anti-oxidants, colorants, and diluents.

The carrier should be acceptable in the sense of being compatible with the other ingredients of the composition and not be deleterious to the recipient. The carrier can be a solid or a liquid, or both, and may be formulated with the compound(s) as a unit-dose composition, for example, a tablet, which can contain from about 0.01% to about 95% by weight of the active compound(s).

The pharmaceutically acceptable carrier can also be selected on the basis of the desired route of administration of the compound(s). The desired route of administration may be one or more of oral, enteral, parenteral, injectable, buccal, and topical. For example, in an embodiment, the carrier is suitable for oral administration. In some embodiments, the composition includes a carrier or additional agent that is suitable for promoting delivery of the compound(s) to the gastrointestinal or intestinal tract.

In particular, the pharmaceutical compositions of the present invention, or compositions in which they are included, can be administered orally, for example, as tablets, coated tablets, dragees, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically acceptable and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch or alginic acid; binding agents, for example starch, gelatin, or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredients are mixed with an inert solid diluent, such as for example calcium carbonate, calcium phosphate or kaolin, or as soft gelatin capsules wherein the active ingredients are present or mixed with water or an oil medium, such as for example peanut oil, liquid paraffin, any of a variety of herbal extracts, milk, or olive oil.

Aqueous suspensions can be produced that contain the active materials in admixture with excipients suitable for the manufacture of aqueous suspensions. Such excipients include suspending agents, such as for example sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, such as for example lecithin, or condensation products of an alkylene oxide with fatty acids, such as for example polyoxyethylene stearate, or condensation products of ethylene oxide with long chain aliphatic alcohols, such as for example heptadecaethyleneoxycetanol, or condensation products of ethylene oxide with partial esters derived from fatty acids and a hexitol, such as for example polyoxyethylene sorbitol monooleate or condensation products of ethylene oxide with partial esters derived from fatty acids and hexitol anhydrides, such as for example polyoxyethylene sorbitan monooleate.

The aqueous suspensions may also contain one or more preservatives, such as for example ethyl or n-propyl p-hydroxybenzoate, one or more coloring agents, one or more flavoring agents, or one or more sweetening agents, such as sucrose, glycerol, sorbitol or saccharin.

Oily suspensions may be formulated by suspending the active ingredients in an omega-3 fatty acid, a vegetable oil, such as for example arachis oil, olive oil, sesame oil or coconut oil, or in a mineral oil such as liquid paraffin. The oily suspensions may contain a thickening agent, such as for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs containing the sulforaphane-cyclodextrin complex may be formulated with sweetening agents, such as for example glycerol, sorbitol, or sucrose. Such formulations may also contain a demulcent, a preservative, and/or flavoring and coloring agents. Liquid dosage forms for oral administration can include pharmaceutically acceptable emulsions, solutions, suspensions, syrups, and/or elixirs containing inert diluents commonly used in the art, such as water. Such compositions may also comprise adjuvants, such as wetting agents, emulsifying and/or suspending agents, and sweetening, flavoring, and/or perfuming agents.

Pharmaceutical compositions suitable for oral administration can be presented in discrete units each containing a predetermined amount of at least one therapeutic compound useful in the present invention; as a powder or granules; as a solution or a suspension in an aqueous or non-aqueous liquid; or as an oil-in-water or water-in-oil emulsion. As indicated, such compositions can be prepared by any suitable method of pharmacy, which may include the step of bringing into association the active compound(s) and the carrier (which can constitute one or more accessory ingredients). In general, the compositions are prepared by admixing the active compound with a liquid or finely divided solid carrier, or both, and then, if necessary, shaping the product.

For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Oral delivery of the combinations of the present invention can include formulations, as are well known in the art, to provide prolonged or sustained delivery of the drug to the gastrointestinal and/or intestinal tract by any number of mechanisms. These include, but are not limited to, pH-sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. For some of the therapeutic compounds useful in the methods, combinations and compositions of the present invention, the intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

In certain embodiments, the pharmaceutical composition may include tablets that may be uncoated or they may be coated by known techniques to delay disintegration and absorption in the gastrointestinal tract and thereby provide a delayed action over a longer period. For example, a time delay material such as glyceryl monostearate or glyceryl distearate may be employed.

In additional embodiments, the compositions created by the subject method may be administered parenterally, such as for example subcutaneously, intravenously, intramuscularly, intrasternally, or by infusion techniques, in the form of sterile injectable aqueous or olageous suspensions. The sterile injectable preparation may also be a sterile injectable solution or suspension in a non-toxic parenterally acceptable diluent or solvent, such as for example a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

Pharmaceutical compositions suitable for parenteral administration can comprise sterile aqueous preparations of a compound of the present invention. These preparations may be administered intravenously, although administration can also be effected by means of subcutaneous, intramuscular, or intradermal injection or by infusion. Such preparations may be prepared by admixing the compound with water and rendering the resulting solution sterile and isotonic with the blood. Injectable compositions according to the invention will generally contain from 0.01 to 10% w/w of a compound disclosed herein.

The active ingredients may also be administered by injection as a composition wherein, for example, saline, dextrose, or water may be used as a suitable carrier. A suitable daily dose of each active therapeutic compound is one that achieves relatively the same blood serum level as produced by oral administration as described above.

Also encompassed by the present invention is buccal or "sub-lingual" administration, which includes lozenges or a chewable gum comprising the compounds set forth herein. The compounds can be deposited in a flavored base and acacia or tragacanth or the compounds may be deposited in pastilles comprising the compounds in an inert base such as gelatin and glycerin or sucrose and acacia.

The pharmaceutical compositions of the present invention are also suitable for topical application to the skin and may take the form of ointments, creams, lotions, pastes, gels, sprays, powders, jellies, collyriums, solutions, suspensions, aerosols, or oils. Carriers may be used and include petroleum jelly (e.g., Vaseline®), lanolin, polyethylene glycols, alcohols, and combinations of two or more thereof. The active compound or compounds are generally present at a concentration of from 0.01 to 50% w/w of the composition, such as for example from about 0.01 to about 2%.

The present invention may also include safe and effective amounts of isotonicity agents, including, salts, such as sodium chloride, and/or non-electrolyte isotonicity agents such as sorbitol and mannitol.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103, available from BASF®), cyclodextrin, or other agents known to those skilled in the art. Such co-solvents may be employed at levels of from about 0.01% to about 2% by weight.

Pharmaceutically acceptable excipients and carriers encompass all the foregoing and the like. Effective formulations and administration procedures are well known in the art and are described in standard textbooks. See e.g. Gennaro, A. R., *Remington: The Science and Practice of Pharmacy*, 20th Edition, (Lippincott, Williams and Wilkins), 2000; Hoover, John E., *Remington's Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., *Handbook of Pharmaceutical Excipients* (3rd Ed.), American Pharmaceutical Association, Washington, 1999.

In the present method, a subject in need of treatment and/or prevention of the disorders described herein and/or related conditions may be treated with an amount of the presently inventive purified sulforaphane, wherein the amount of the individual components provides a dosage or amount that is sufficient to constitute a treatment or prevention effective amount.

The effective amount of purified sulforaphane-cyclodextrin complex, of course, depend on a number of factors, such as the specific compound chosen, the use for which it is intended, the mode of administration, the host to be treated, and the clinical condition of the recipient.

A carcinogenic, tumorigenic, or anti-bacterial symptom is considered ameliorated or improved if any benefit is achieved, no matter how slight.

Dosages for the present compositions and methods provided herein may be determined and adjusted based on the efficacy demonstrated in providing a chemoprotective or chemopreventative result. In addition, one of ordinary skill in the art will know how to measure and quantify the presence or absence of carcinogenesis or tumorigenesis symptoms.

Dosages for the present compositions are those that are effective to provide a chemoprotective, chemopreventative, and/or anti-bacterial effect.

Those skilled in the art will appreciate that dosages may also be determined with guidance from Goodman & Gilman's *The Pharmacological Basis of Therapeutics*, Ninth Edition (1996), Appendix II, pp. 1707-1711.

EXAMPLES

The invention will now be illustrated in the following Examples.

General Materials and Methods $^1$H and $^{13}$C NMR spectra were recorded on a Oxford 400 MHz spectrometer using TMS as the internal standard and the chemical shifts are reported in ppm.

Electrospray ionization mass spectrometry (ESI-MS) was performed on a Micromass Platform LCZ connected to Waters 2695 separations module and Water 996 photodiode array detector. GC-MS spectrometry was performed on a Agilent 7820A/5975 MSD series.

HPLC was performed on a HP 1050 Module, Column: Phenomenex Gemini C18, 5μ, 110 A°, 250×4.6 mm. Total run time: 40 min. MeCN in H2O+0.1% TFA. Flow: 1.5 mL/min. Detector: 244 nm (VWD).

Karl Fischer (H$_2$O content) analysis was performed on a KF coulometer 831 equipped with Ti stand 703.

All reactions were run under an atmosphere of dry nitrogen and the reported yields are isolated yields. All chemical reagents were purchased from commercial sources and used as received.

Preparation of Starting Materials

Preparation of 1-Isothiocyanato-4-Methylthiobutane (Formula A)

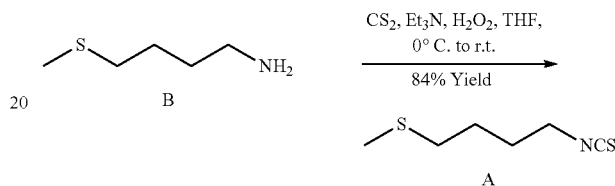

A 50-L multi-neck round bottom flask equipped with an overhead stirrer, a temperature probe and a 1 L addition funnel and a positive flow of N$_2$ was cooled to −10° C. in MeOH/ice bath and charged with THF (EMD, reagent grade, 15.0 L). 1-Amino-4-methylthiobutane (Formula B; 1.5 Kg, 12.6 moles, 1.0 equiv.) and triethylamine (1.75 L, 1.0 equiv.) were added, and the solution was further stirred until it had cooled below −10° C. Carbon disulfide (755 mL, 1.0 equiv.) was added dropwise over 2 hours while keeping the internal temperature below −3° C. (bath temperature was −20° C.), after which the yellow-green solution had been warmed to 11° C. Hydrogen peroxide (35% aq, 1224 mL, 1.0 equiv.) was added slowly over 2.5 hours while keeping the internal temperature between 11 to 18° C. (bath temperature was 0° C.), which produced a dark orange-red suspension with swirling yellow particulates.

Workup:

After stirring overnight, an aliquot was checked by GC (75° C.→200 at 15°/min, then 40°/min to 300, 2 min hold: 7.73 mins) and then the mixture was transferred into a 50-L workup station using a hose equipped with a filter head. The mixture was diluted with 4.5 L of ethyl acetate, and then washed with 10% HCl (6 L), water (6 L), and brine (7.5 L). The collected organic layer was dried over anhydrous Na$_2$SO$_4$, filtered and concentrated under vacuum to yield ~2 kg of dark red oil.

Distillation:

The red oil was transferred into a 2 L (3 batches) round bottom flask and connected to the Kugelrohr. The apparatus was placed under high vacuum (~0.3-0.5 torr), and the air bath heated to 85° C. The forerun (mostly ethyl acetate and trace unknown by-product) was discarded. After changing the receiver, the bath temperature was increased to 115° C. Pale yellow material distilled over at 100-110° C., and immediately froze upon contact with the dry-ice/acetone bath. After distillations (three batches) yielded 1.7 Kg (84% yield) material at 98% pure by HPLC and >99% pure by GC.

$^1$HNMR (CDCl$_3$, 400 MHz); δ1.7-1.85 (m, 4H), 2.2 (s, 3H), 2.55 (t, 2H), 3.56 (t, 2H)

Example 1

Preparation of Sulforaphane (1-Isothiocyanato-4-Methylsulfinylbutane)

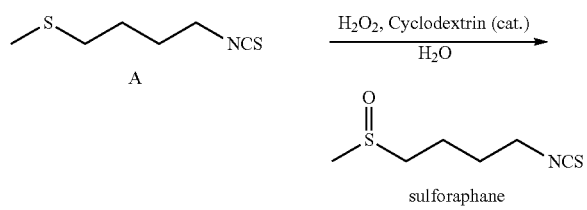

A 5-L multi-neck round bottom flask equipped with an overhead stirrer, a temperature probe and a 500 mL addition funnel was set-up with a positive flow of $N_2$. α-Cyclodextrin (30 g, 0.03 moles, 0.01 equivalents) was dissolved in 1 L of distilled water and degassed over 30 minutes by purging with nitrogen. To the above solution was added 501 g (3.1 moles, 1 equivalent) of 1-isothiocyanato-4-methylthiobutane (Formula A) and degassed again at 0° C. over 30 minutes. To this biphasic reaction mixture was added 305 mL of $H_2O_2$ (3.1 moles, 1 equivalent, 35% aq.) slowly while maintaining temperature between 0-2° C. [NOTE: Peroxide was dropped in at a rate sufficiently low so that the temperature did not increase above 10° C.]. Once the addition complete, the reaction mixture was stirred at ice bath temperature for about 8 hours and then slowly allowed to come to room temperature overnight. Reaction mixture was filtered to remove the light yellow insoluble solids and then filtrate was kept in the refrigerator for ~1 h. Based on the analytical HPLC the crude sulforaphane was ~95% pure.

This material was used for the complexation step (Example 2) without any further workup/purification.

Summary of Three Repetitions—

| Lot | Reaction size | Purity by HPLC (crude) | Observations |
| --- | --- | --- | --- |
| 1 | 501 g | 95% | $H_2O_2$ was added at <2° C. |
| 2 | 500 g | 95.6%. | $H_2O_2$ was added at <4° C. |
| 3 | 500 g | 95.4% | $H_2O_2$ was added at <2° C. |

All three batches were conducted at the same reaction scale and the reactions proceeded in similar way in terms of reaction time and product purity.

$^1$HNMR (CDCl$_3$, 400 MHz); δ1.90 (m, 4H), 2.58 (s, 3H), 2.75 (m, 2H), 3.60 (t, 2H).

$^{13}$CNMR (CDCl$_3$, 100 MHz); δ130.2, 53.4, 44.5, 38.5, 29.5, 20.1

Example 2

Preparation of Sulforaphane-Cyclodextrin Complex

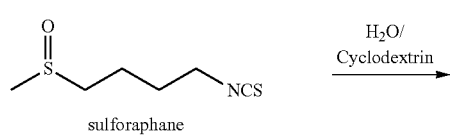

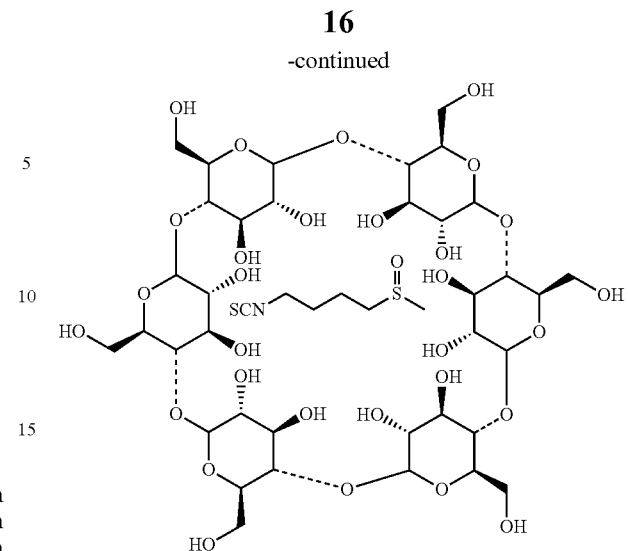

α-Cyclodextrin (Wacker CAVAMAX W6 Food Grade, 3015 g, 3.1 moles, 1 equivalent) was dissolved in distilled water (8 L) by heating up to 55° C. under nitrogen atmosphere. The homogeneous solution was cooled down to ~25° C. using an ice-water bath and then degassed for ~20 min by purging nitrogen. After degassing, it turned into a foggy solution. Aqueous solution of sulforaphane was removed from the refrigerator (see previous step) and then added to the above foggy α-cyclodextrin solution at once. At this stage reaction temperature was ~18° C., and continued stirring at room temperature overnight (~16 h). The heterogeneous reaction mixture was cooled down to 1-2° C. using ice-methanol bath and stirred for 3 hr at that temperature. The precipitated white solid was filtered and dried overnight under high vacuum at room temperature by covering the filter funnel with a latex sheet. The white filter cake was transferred into a 10-L rotovap flask and dried further at room temperature under a high vacuum to afford 2,802 g of complex (98.7% pure by HPLC, 78.5% yield).

Summary of Three Repetitions—

| Lot | Reaction size** | Purity by HPLC | Yield* |
| --- | --- | --- | --- |
| 1 | 550.8 g | 98.5% | 78.5% |
| 2 | 549.7 g | 98.6% | 76.9% |
| 3 | 549.7 g | 98.7% | 73.2% |

*overall yield in last two steps,
**based on the 100% conversion in the previous step.

All three batches were conducted at almost same scale and the reactions proceeded in similar way in terms of reaction time, yield, product purity and percentage loading of sulforaphane on α-cyclodextrin $^1$HNMR (D$_2$O, 400 MHz); δ1.99 (br, 4H), 2.73 (s, 3H), 2.98 (br, 2H), 3.60 (m, 12H), 3.70 (br, 2H), 3.92 (m, 24H), 5.11 (d, 6H).

$^{13}$CNMR (D$_2$O, 100 MHz); δ130.05, 101.82, 81.40, 74.05, 71.98, 71.84, 60.34, 52.02, 44.94, 37.03, 29.29, 20.08.

Example 3

Preparation of Sulforaphane (1-Isothiocyanato-4-Methylsulfinylbutane) with Different Catalysts and Reaction Conditions General Procedure:

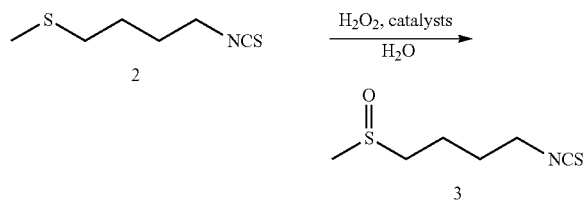

A multi-neck round bottom flask equipped with an overhead stirrer, a temperature probe and an addition funnel was set-up with a positive flow of $N_2$. Acid catalyst (0.001 to 0.01 equivalents) was dissolved in solvent (water, acetonitrile, acetone etc.) and degassed over 30 minutes by purging with nitrogen. To the above solution was added 1 equivalent of thioether starting material (2) and degassed again at 0-5° C. over 30 minutes. To this biphasic reaction mixture was added 1 equivalent of oxidizing agent ($H_2O_2$, m-CBPA etc.) slowly while maintaining temperature between 0-10° C. Once the addition complete, the reaction mixture was stirred at ice bath temperature for about 8-24 hours and then slowly allowed to come to room temperature overnight. Reaction mixture was filtered to remove the insoluble solids and then the filtrate was kept in the refrigerator or used immediately in the following step. Based on the analytical HPLC the crude sulforaphane was ≥95% pure. This material was used for the complexation step without any further purification.

The oxidation of compound 2 into sulforaphane in various solvents and/or in the presence of different catalysts/acids are shown in the Table below, along with the reaction conditions.

| Reaction Conditions | $H_2O_2/H_2O$, Acetone, 0° C. to RT | $H_2O_2$, $H_2O$, Acetonitrile 0° C. to RT | $H_2O_2/H_2O$, 0.1 eq α-CD 0° C. to RT | $H_2O_2/H_2O$, 0.01 eq α-CD, 0° C. to RT | $H_2O_2/H_2O$, 1.0 eq α-CD, 0° C. to RT | $H_2O_2/H_2O$ 0.05 eq AcOH 0° C. to RT | $H_2O_2/H_2O$ 0.1% Fuller's Earth |
|---|---|---|---|---|---|---|---|
| Purity by HPLC | 95.6% (3.1% SM) | 96.8% (0.7% SM) | 96% (1% SM) | 98% (0.5% SM) | 77% (2.1% SM) | 98.8% (0.06% SM) | 98% (0.06% SM) |
| Yield | Not isolated | Not isolated | Not isolated | 82%* | Not isolated | Not isolated | Not isolated |
| Final purity | — | — | — | 98% | — | — | — |

*Isolated yield.

Based on the above results, all of the listed catalysts produced similar results, but cyclodextrin is preferred since it is used in the next complexation step to stabilize the sulforaphane.

Only trace amount of sulfonyl impurity (Erysolin) was detected by HPLC.

The invention claimed is:

1. A process for the preparation of a complex of sulforaphane and cyclodextrin, the process comprising:
    (i) reacting, in an aqueous solvent, a compound of formula A:

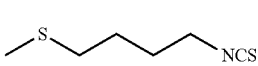

with an oxidizing agent and in the presence of a catalyst to form sulforaphane; and
    (ii) mixing the sulforaphane from step (i) with cyclodextrin in an aqueous solvent to form a precipitate of the sulforaphane-cyclodextrin complex, wherein the oxidizing agent is hydrogen peroxide or a water soluble or miscible organic per-acid, or a mixture thereof.

2. A process according to claim 1, wherein the solvent used in step(i) and step(ii) is water.

3. A process according to claim 1, wherein the oxidizing agent is hydrogen peroxide.

4. A process according to claim 1, wherein the catalyst is selected from cyclodextrin and organic or inorganic acids.

5. A process according to claim 4, wherein the catalyst is a cyclodextrin.

6. A process according to claim 5, wherein the catalyst is alpha-cyclodextrin.

7. A process according to claim 1, wherein 0.0001 to 1.0 molar equivalents of catalyst are present (relative to the compound of formula A).

8. A process according to claim 1, wherein in step (i) the temperature of the reaction is maintained at a temperature of 25° C. or less or 15° C. or less when the oxidizing agent is added to the reaction mixture.

9. A process according to claim 1, wherein the cyclodextrin used in step (ii) is selected from one or more of W6 (alpha) cyclodextrin (a six sugar ring molecule), W7 (beta) cyclodextrin (a seven sugar ring molecule), W8 (gamma) cyclodextrin (an eight sugar ring molecule), derivatives thereof, and mixtures thereof.

10. A process according to claim 9, wherein the cyclodextrin used in step (ii) is alpha-cyclodextrin.

11. A process according claim 10, wherein the mixture is cooled to a temperature within the range of about −8° C. to about 10° C.

12. A process according claim 10, wherein the mixture is cooled to a temperature within the range of about −5° C. to about 4° C.

13. A process according to claim 10, wherein the molar ratio of sulforaphane to cyclodextrin in the resultant complex is within the range of 0.4:1 to 1:1.

14. A process according to claim 1, wherein the process comprises a further step of recystallizing the resulting complex.

15. A process according to claim 1, wherein the catalyst is selected from ascorbic acid, formic acid, acetic acid, and/or sulphuric acid.

16. A process for the preparation of a complex of sulforaphane and cyclodextrin, the process comprising:

(i) reacting, in an aqueous solvent, a compound of formula A:

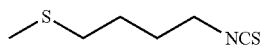

with an oxidizing agent and in the presence of a catalyst to form sulforaphane; and (ii) mixing the sulforaphane from step (i) with cyclodextrin in an aqueous solvent to form a precipitate of the sulforaphane-cyclodextrin complex, wherein the catalyst is selected from cyclodextrin and organic or inorganic acids.

17. A process according to claim 16, wherein the solvent used in step(i) and step(ii) is water.

18. A process according to claim 16, wherein the oxidizing agent is hydrogen peroxide.

19. A process according to claim 16, wherein the catalyst is a cyclodextrin.

20. A process according to claim 19, wherein the catalyst is alpha-cyclodextrin.

21. A process according to claim 16, wherein 0.0001 to 1.0 molar equivalents of catalyst are present (relative to the compound of formula A).

22. A process according to claim 16, wherein in step (i) the temperature of the reaction is maintained at a temperature of 25° C. or less or 15° C. or less when the oxidizing agent is added to the reaction mixture.

23. A process according to claim 16, wherein the cyclodextrin used in step (ii) is selected from one or more of W6 (alpha) cyclodextrin (a six sugar ring molecule), W7 (beta) cyclodextrin (a seven sugar ring molecule), W8 (gamma) cyclodextrin (an eight sugar ring molecule), derivatives thereof, and mixtures thereof.

24. A process according to claim 23, wherein the cyclodextrin used in step (ii) is alpha-cyclodextrin.

25. A process according claim 24, wherein the mixture is cooled to a temperature within the range of about −8° C. to about 10° C.

26. A process according to claim 24, wherein the mixture is cooled to a temperature within the range of about −5° C. to about 4° C.

27. A process according to claim 24, wherein the molar ratio of sulforaphane to cyclodextrin in the resultant complex is within the range of 0.4:1 to 1:1.

28. A process according to claim 16, wherein the process comprises a further step of recystallizing the resulting complex.

29. A process according to claim 16, wherein the catalyst is selected from ascorbic acid, formic acid, acetic acid, and/or sulphuric acid.

* * * * *